(12) United States Patent
Case et al.

(10) Patent No.: US 7,686,844 B2
(45) Date of Patent: Mar. 30, 2010

(54) PROSTHETIC VALVE FOR IMPLANTATION IN A BODY VESSEL

(75) Inventors: Brian C. Case, Bloomington, IN (US); Thomas A. Osborne, Bloomington, IN (US); Jacob A. Flagle, Bloomington, IN (US); Fred T. Parker, Unionville, IN (US)

(73) Assignee: Cook Incorporated, Bloomington, IN (US)

( * ) Notice: Subject to any disclaimer, the term of this patent is extended or adjusted under 35 U.S.C. 154(b) by 354 days.

(21) Appl. No.: 10/903,907

(22) Filed: Jul. 30, 2004

(65) Prior Publication Data

US 2005/0085900 A1    Apr. 21, 2005

Related U.S. Application Data

(60) Provisional application No. 60/491,745, filed on Jul. 31, 2003.

(51) Int. Cl.
  *A61F 2/06*    (2006.01)
  *A61F 2/24*    (2006.01)

(52) U.S. Cl. .................. 623/1.24; 623/1.26; 623/2.14; 623/2.18

(58) Field of Classification Search .......... 623/1.1, 623/1.13, 1.23–1.26, 1.44, 2.1–2.42, 1.11–1.15; 606/194, 200
See application file for complete search history.

(56) References Cited

U.S. PATENT DOCUMENTS

| | | | |
|---|---|---|---|
| 4,470,157 A * | 9/1984 | Love ........................ 623/2.15 |
| 4,580,568 A | 4/1986 | Gianturco | |
| 4,666,442 A * | 5/1987 | Arru et al. ................. 623/2.13 |
| 5,411,552 A * | 5/1995 | Andersen et al. ........... 623/2.18 |
| 5,545,215 A * | 8/1996 | Duran ....................... 623/1.26 |
| 5,667,523 A * | 9/1997 | Bynon et al. ............... 623/1.13 |
| 5,855,601 A * | 1/1999 | Bessler et al. .............. 623/2.38 |
| 6,126,686 A * | 10/2000 | Badylak et al. ............ 623/1.24 |
| 6,231,598 B1 | 5/2001 | Berry et al. | |
| 6,299,635 B1 | 10/2001 | Frantzen | |
| 6,312,465 B1 * | 11/2001 | Griffin et al. ............... 623/2.38 |
| 6,375,679 B1 * | 4/2002 | Martyn et al. .............. 623/2.12 |
| 6,464,720 B2 | 10/2002 | Boatman et al. | |
| 6,494,909 B2 | 12/2002 | Greenhalgh | |
| 6,508,833 B2 | 1/2003 | Pavcnik et al. | |
| 2001/0039450 A1 | 11/2001 | Pavcnik et al. | |
| 2003/0055492 A1 | 3/2003 | Shaolian et al. | |
| 2003/0153974 A1* | 8/2003 | Spenser et al. ............. 623/2.11 |
| 2004/0102855 A1 | 5/2004 | Shank | |

FOREIGN PATENT DOCUMENTS

WO    WO 0154625 A1 *    8/2001

* cited by examiner

*Primary Examiner*—Anhtuan T Nguyen
*Assistant Examiner*—Kathleen Sonnett
(74) *Attorney, Agent, or Firm*—Buchanan Intellectual Property Office LLC (57) ABSTRACT

Prosthetic valves for implantation in a body vessel are provided. Prosthetic valves according to the invention comprise first and second frame members and a graft member at least partially disposed between the first and second frame members. The graft member forms a valve that permits fluid flow through the body vessel in a first direction and substantially prevents fluid flow through the body vessel in a second, opposite direction.

14 Claims, 9 Drawing Sheets

PROSTHETIC VALVE FOR IMPLANTATION IN A BODY VESSEL

CROSS-REFERENCE TO RELATED APPLICATION

This application claims priority to U.S. Provisional Application Ser. No. 60/491,745 filed on Jul. 31, 2003. The entire disclosure of which is hereby incorporated into this disclosure in its entirety.

FIELD OF THE INVENTION

The invention relates to implantable medical devices. More specifically, the invention relates to prosthetic valves for implantation in a body vessel.

BACKGROUND OF THE INVENTION

Many vessels in animals transport fluids from one bodily location to another. Frequently, fluid flows in a unidirectional manner long the length of the vessel. Varying fluid pressures over time, however, can introduce a temporary reverse flow direction in the vessel. In some vessels, such as mammalian veins, natural valves are positioned along the length of the vessel and act as one-way check valves that open to permit the flow of fluid in the desired direction, and quickly close upon a change in pressure, such as a transition from systole to diastole, to prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the leaflets to close. Furthermore, the natural valve leaflets may become damaged, such as by formation of thrombus and scar tissue, which may also affect the ability of the valve leaflets to close. Once a valve is damaged, venous valve insufficiency may be present, and can lead to discomfort and possibly ulcers in the legs and ankles.

Current treatments for venous valve insufficiency include the use of compression stockings that are placed around the leg of a patient. Surgical techniques are also employed in which valves can be bypassed, removed, or replaced with autologous sections of veins that include competent valves.

Minimally invasive techniques and instruments for placement of intralumenal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents in the U.S. market in the early 1990's. Coronary and peripheral stents have been proven to provide a superior means of maintaining vessel patency, and have become widely accepted in the medical community. Furthermore, the use of stents has been extended to treat aneurisms and to provide occlusion devices, among other uses.

Recently, prosthetic valves have been developed that include a support frame such as a stent. In these devices, a graft member can be attached to the support frame to provide a valve function to the device. For example, the graft member can be in the form of a leaflet that is attached to a stent and movable between first and second positions. In a first position, the valve is open and allows fluid flow to proceed through a vessel in a first direction, and in a second position the valve is closed to prevent fluid flow in a second, opposite direction. An example of this type of prosthetic valve is described in commonly owned U.S. Pat. No. 6,508,833, to Pavcnik for a MULTIPLE-SIDED INTRALUMINAL MEDICAL DEVICE, which is hereby incorporated by reference in its entirety. In other examples of prosthetic valves, a tube that terminates in leaflets is attached to a support frame to form a valve. The leaflets open to permit fluid flow in a first direction and close to prevent fluid flow in a second, opposite direction. An example of this configuration is provided in U.S. Pat. No. 6,494,909 to Greenhalgh for AN ENDOVASCULAR VALVE, which is hereby incorporated by reference in its entirety.

SUMMARY OF EXEMPLARY EMBODIMENTS OF THE INVENTION

The invention provides medical devices for implantation in a body vessel. Medical devices according to exemplary embodiments of the invention comprise first and second frame members and a graft member forming a valve that permits fluid flow through a body vessel in a first direction, and substantially prevents fluid flow through the body vessel in a second, opposite direction At least a portion of the graft member is disposed between the frame members.

In one exemplary embodiment, a prosthetic valve according to the invention comprises first and second tubular frame members and a graft member disposed between the frame members. The second tubular frame member is circumferentially disposed around the first tubular frame member. The graft member forms a valve that permits fluid flow through a body vessel in a first direction and substantially prevents fluid flow through the body vessel in a second, opposite direction.

In another exemplary embodiment, a prosthetic valve according to the invention comprises first and second tubular frame members and a graft member disposed between the frame members. The first tubular frame member defines axially-extending extension points and the second tubular frame member is circumferentially disposed around the first tubular frame member. The graft member is attached to the extension points of the first tubular frame member and forms a valve that permits fluid flow through a body vessel in a first direction and substantially prevents fluid flow through the body vessel in a second, opposite direction.

In another exemplary embodiment, a prosthetic valve according to the invention comprises first and second tubular frame members and a tubular graft member. The first tubular frame member defines first and second axially-extending extension points, and the second tubular frame member is circumferentially disposed around the first tubular frame member. The second tubular frame member defines a sinus portion. The graft member has a first portion disposed on an external surface of the second tubular frame member, and a second portion disposed between the first and second tubular frame members. The second portion is attached to the extension points of the first tubular frame member, and forms a valve that permits fluid flow through a body vessel in a first direction and substantially prevents fluid flow through the body vessel in second, opposite direction.

In another exemplary embodiment, a prosthetic valve according to the invention comprises first and second frame members and a graft member. In this embodiment, ends of the frame members overlap and a portion of the graft member is disposed between the overlapping ends. Another portion of the graft member is disposed radially inward of another end of the second frame member and forms a valve that permits fluid flow through a body vessel in a first direction and substantially prevents fluid flow through the body vessel in a second, opposite direction.

In another exemplary embodiment, a prosthetic valve according to the invention comprises first and second tubular frame members and a tubular graft member. An end of the second tubular frame member is disposed circumferentially around an end of the first tubular frame member to form an overlap region. A portion of the tubular graft member is disposed on a portion of an external surface of the first tubular frame member and another portion of the tubular graft member is disposed between the first and second tubular frame members at the overlap region. A third portion of the graft member is attached to a portion of the internal surface of the second tubular frame member and forms a valve that permits fluid flow through a body vessel in a first direction and substantially prevents fluid flow through the body vessel in a second, opposite direction.

The invention also provides methods of making prosthetic valves for implantation in a body vessel. One method according to the invention comprises providing a first frame member, providing a second frame member, providing a graft member, disposing at least a portion of the graft member between the first and second frame members, and forming a valve with the graft member.

The invention also provides methods of implanting a prosthetic valve in a body vessel. One method according to the invention comprises providing a prosthetic valve comprising first and second frame members and a graft member disposed between the first and second frame members and forming a valve; percutaneously delivering the prosthetic valve through a body vessel to a point of treatment; and deploying the prosthetic valve at the point of treatment.

Another method of implanting a prosthetic valve according to the invention comprises providing a first frame member; providing a second frame member with an attached graft member that forms a valve; percutaneously delivering the first frame member through a body vessel to a point of treatment; deploying the first frame member at the point of treatment; percutaneously delivering the second frame member to the point of treatment; and deploying the second frame member.

Additional understanding of the invention can be obtained with review of the description of exemplary embodiments appearing below and reference to the appended drawings.

DETAILED DESCRIPTION OF EXEMPLARY EMBODIMENTS OF THE INVENTION

The following provides a detailed description of various exemplary embodiments of the invention. The embodiments described and illustrated herein are exemplary in nature, and serve simply as examples to aid in enabling one of ordinary skill in the art to make and use the invention. The description of exemplary embodiments is not intended to limit the invention, or its protection, in any manner.

The invention provides prosthetic valves for use in a body vessel, such as the human vasculature. Prosthetic valves according to the invention comprise first and second frame members and a graft member forming a valve that permits fluid flow through a body vessel in a first direction and substantially prevents fluid flow through the body vessel in a second, opposite direction. At least a portion of the graft member is disposed between the frame members. The inclusion of two frame members in the prosthetic valves of the invention is expected to provide a stable structure for the valves under typical loads for a particular application. Also, it is believed that the inclusion of two frame members will provide a separation between one or more portions of the graft member and an interior wall of a body vessel in which the prosthetic valve is implanted. This separation may protect portions, such as valve leaflets, of graft members formed of certain materials, such as extracellular matrix (ECM) materials, from incorporation into the vessel wall.

Medical devices according to the invention can be used as a valve in a variety of body vessels, including within the heart, digestive tract, and other body vessels. Exemplary embodiments of the invention are particularly well suited for use as percutaneously delivered prosthetic venous valves.

Figures 1, 2:
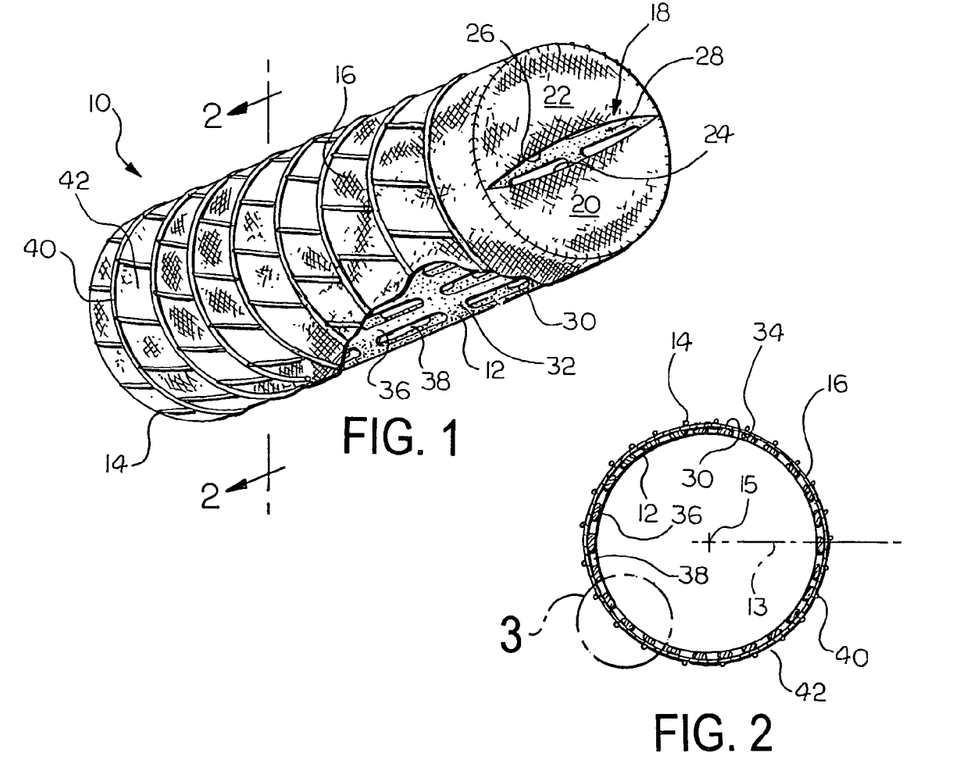
FIG. 1 is a perspective view, partially broken away, of a prosthetic valve according to a first exemplary embodiment of the invention.
FIG. 2 is a cross-sectional view of the prosthetic valve illustrated in FIG. 1, taken along line 2-2.
Figure 3:
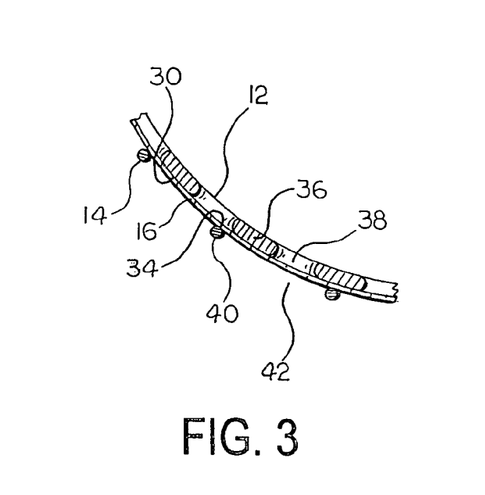
FIG. 3 is a magnified view of area 3 in FIG. 2.

FIGS. 1 through 3 illustrate a prosthetic valve 10 according to a first exemplary embodiment of the invention. In this embodiment, the prosthetic valve 10 comprises a first frame member 12, a second frame member 14, and a graft member 16 partially disposed between the first 12 and second 14 frame members. As best illustrated in FIG. 2, the second frame member 14 is disposed radially outward from the first frame member 12. That is, the second frame member 14 intersects a hypothetical radial line 13 extending from a hypothetical central point 15 and through the frame members 12, 14 at a point further from the central point 15 than a point at which the first frame member 12 intersects the line 13. In this embodiment, the first 12 and second 14 frame members comprise tubular members, and the first frame member 12 is disposed within a lumen defined by the second frame member 14. Thus, the second frame member 14 is disposed circumferentially around the first frame member 12. Also in this embodiment, as best illustrated in FIG. 1, the first 12 and second 14 frame members have substantially the same axial lengths.

The first 12 and second 14 frame members comprise structural bodies having one or more surfaces. The first frame member 12 has an exterior surface 30 that can include an adhesive 32 or other means for attaching the graft member 16 to the frame member 12. Any suitable means for attaching two members can be used, and specific, non-limiting examples include sutures, clips, metal and plastic bands, barbs, weld joints, and other attachment elements. The second frame member 14 has an interior surface 34 that may also include an adhesive or other means for attaching (not illustrated in FIGS. 1 through 3) the graft member 16 to the second frame member 14.

Each of the frame members 12, 14 can comprise any suitable frame that provides the desired surfaces between which a portion of the graft member 16 can be disposed. As best illustrated in FIGS. 1 and 2, each frame member 12, 14 can comprise a tubular frame member. Medical stents provide tubular frame members, and any suitable medical stent can be used in the prosthetic valves of the invention. It is noted, though, that the frame member(s) need not provide a stenting function; such a function is optional. If one or more stents are used in a prosthetic valve according to the invention, the stent can be any suitable type of stent, including a wire frame member, a solid tubular member, a tubular member with openings cut therein, or any other suitable medical stent. Examples of suitable stents for use in the prosthetic valves of the invention include the stents described in U.S. Pat. No. 6,508,833 to Pavcnik et al. for a MULTIPLE-SIDED INTRALUMINA MEDICAL DEVICE; U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and Published Application for United States Patent 20010039450 to Pavcnik et al. for an IMPLANTABLE MEDICAL DEVICE, all of which are hereby incorporated by reference in their entirety for the purpose of describing suitable stents for use in the invention.

To facilitate delivery of the prosthetic valves of the invention, one or both of the frame members 12, 14 can be expandable members, such as expandable stents. Expandable stents have two configurations: a first, unexpanded configuration in which the stent has a reduced diameter and a second, expanded configuration in which the stent has an expanded diameter. The unexpanded configuration provides a small profile to the stent, which facilitates advancement and navigation of the stent through a body vessel, such as during percutaneous delivery to a point of treatment in a body vessel. In the expanded configuration, the stent has a larger diameter, which allows the stent to interact with the interior wall of the body vessel. Expandable stents can be self-expandable or may require the application of an outwardly-directed expansile force to induce expansion, such as inflation of an underlying balloon.

In the embodiment illustrated in FIGS. 1 through 3, the first frame member 12 comprises a balloon-expandable stent cut from a solid tube. The second frame member 14 comprises a self-expandable stent comprising a wire frame member. The first frame member 12 in this embodiment comprises a series of interconnected struts 36 and openings 38. The struts 36 comprise the material of the tube left after cutting, while the openings 38 comprise the spaces left following removal of material during cutting of the tube. The second frame member 14 comprises a plurality of struts 40 interconnected to define a plurality of openings 42. The second frame member 14 of this embodiment comprises a wire frame stent, which may be formed from one or more wires by braiding, weaving, or other suitable techniques.

In prosthetic valves according to the invention, the first and second frame members 12, 14 can comprise the same types of frame members. For example, both frame members can be self-expandable or both can be balloon-expandable. A combination of different types of frame members can also be used. For example, as illustrated in FIGS. 1 through 3, the first frame member 12 can be a balloon-expandable stent and the second frame member 14 can be a self-expandable stent. In embodiments in which the second, or outer, frame member is self-expandable, it may be advantageous to attach the self-expandable frame member to the graft member, the first, or inner, frame member, or both using any suitable means for attaching members, as described above. This attachment is expected to allow the prosthetic valve to be deployed as a single unit in a single step. If such deployment is not desired, this attachment is not necessary.

Figure 4:
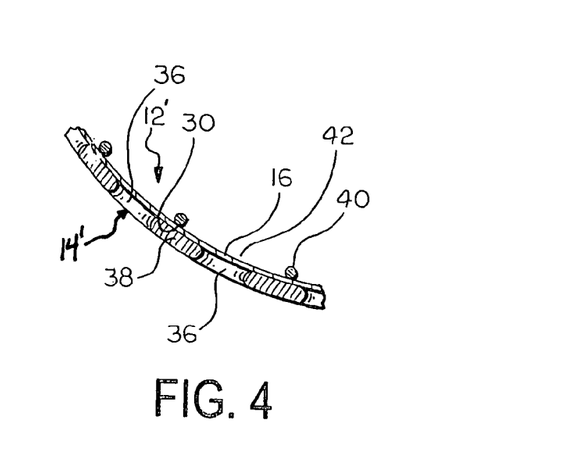
FIG. 4 is a magnified view of a prosthetic valve according to an alternative embodiment of the invention.

In an alternative embodiment, illustrated in FIG. 4, the first frame member 12' is a self-expandable stent and the second frame member 14' is a balloon-expandable stent.

As described more fully below, the graft member 16 can be attached to one or both of the frame members 12, 14, or can be retained between the frame members 12, 14 by friction alone. Frictional retention of the graft member 16 can be enhanced by using frame members 12, 14 of appropriate dimension. For example, the second frame member 14 can have a resting outer diameter that is slightly larger than an inner diameter of a vessel in which the device will be implanted at a point of treatment. As used herein, the term "resting outer diameter" refers to an outer diameter of a member when the member is free of any constraining force applied by another member or other external factor. The first frame member 12 can also have a resting outer diameter that is slightly larger than a resting inner diameter of the second frame member 14. These configurations of the frame members 12, 14 will ensure that a force will be exerted upon a member disposed between the frame members 12, 14, such as the graft member 16, thereby enhancing frictional retention of the member.

A wide variety of materials acceptable for use as the graft member 16 are known in the art, and any suitable material can be used. The material chosen need only be able to perform as described herein, and be biocompatible, or be able to be made biocompatible. Examples of suitable materials for the graft member 16 include natural materials, synthetic materials, and combinations thereof. Examples of suitable natural materials include extracellular matrix (ECM) materials, such as small intestine submucosa (SIS), and other bioremodellable materials, such as bovine pericardium. Other examples of ECM materials that can be used for the graft member 16 include stomach submucosa, liver basement membrane, urinary bladder submucosa, tissue mucosa, and dura mater. Examples of suitable synthetic materials include polymeric materials, such as expanded polytetrafluroethylene and polyurethane. ECMs are particularly well suited materials for use in the graft member, at least because of their abilities to remodel and become incorporated into adjacent tissues. These materials can provide a scaffold onto which cellular in-growth can occur, eventually allowing the material to remodel into a structure of host cells.

Figure 5:
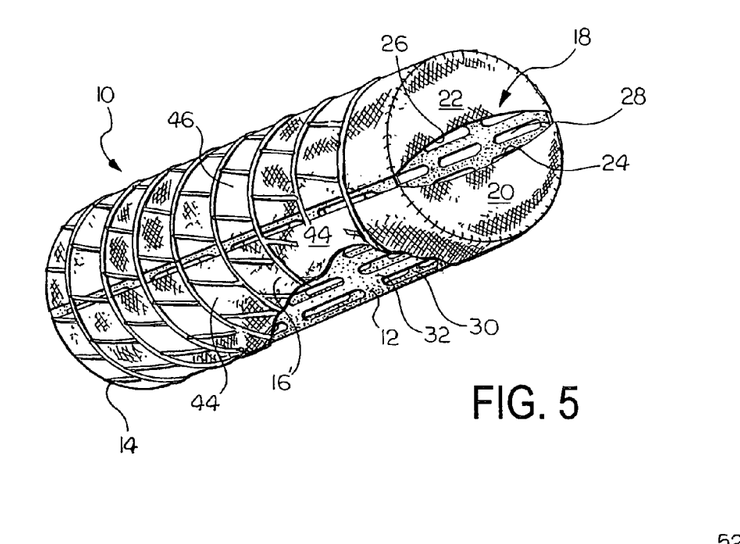
FIG. 5 is a perspective view, partially broken away, of a prosthetic valve according to a second exemplary embodiment of the invention.

The graft member 16 can be a tubular member, as illustrated in FIGS. 1 and 2, or may have any other suitable configuration. For example, in the exemplary embodiment illustrated in FIG. 5, the graft member 16' comprises first 44 and second 46 graft members. In this embodiment, both the first 44 and second 46 graft members are sheets of material disposed between the first 12 and second 14 frame members. The first 44 and second 46 graft members each have semi-circular configurations and can be connected to each other, or can be independently disposed between the frame members 12, 14. The first graft member 44 has a portion 20 with an edge 24 that cooperates with an edge 26 of a portion 22 of the second graft member 46 to define the opening 28 of the valve 18. The specific form chosen for the graft member 16 will depend on several factors, including the form of the valve 18 and the mechanism by which the first 12 and/or second 14 frame members retain the graft member 16. In another alternative embodiment, the graft member comprises a single sheet. In this embodiment, the sheet can be rolled so that edges are adjacent each other, or can be held in relative position by compression of the graft between first and second frame members, such as tubular first and second frame members. In all embodiments, at least a portion of the graft member 16 is disposed between at least a portion of the first frame member 12 and at least a portion of the second frame member 14.

The graft member 16 can be retained by one or both of the frame members 12, 14 by friction alone, as described above, or by any other suitable retention mechanism. For example, the graft member 16 can be attached to one or both of the frame members 12, 14. In embodiments in which the graft member 16 is attached to one or both of the frame members 12, 14, any suitable means for attaching two members can be used, and specific, non-limiting examples include sutures, clips, metal and plastic bands, barbs, weld joints, and other attachment elements. The specific means for attaching chosen will depend on several factors, including the nature of the frame member to which the graft member is being attached and the nature of the graft member itself. Sutures provide an acceptable means for attaching a graft member comprising SIS or other ECM material to a metal or plastic frame member.

The graft member 16 forms a valve 18. When a prosthetic valve according to the invention is implanted in a body vessel, the valve 18 permits fluid flow through the body vessel in a first direction, and substantially prevents fluid flow through the body vessel in a second, opposite direction. The valve 18 can be any suitable type of valve that can be formed by the graft member 16. As illustrated in FIG. 1, the valve 18 can comprise an end portion of a tubular graft member 16 that spans an end of the first frame member 12 in a drum-like fashion. First 20 and second 22 portions of the graft member 16 have first 24 and second 26 edges, respectively, that cooperatively define an opening 28. The opening 28 opens to permit fluid flow through the body vessel in the first direction, and closes to substantially prevent fluid flow through the body vessel in a second, opposite direction. It is believed that the opening 28 alternates between the open and closed configurations in response to changes in fluid direction and/or pressure within the body vessel.

Figure 6:
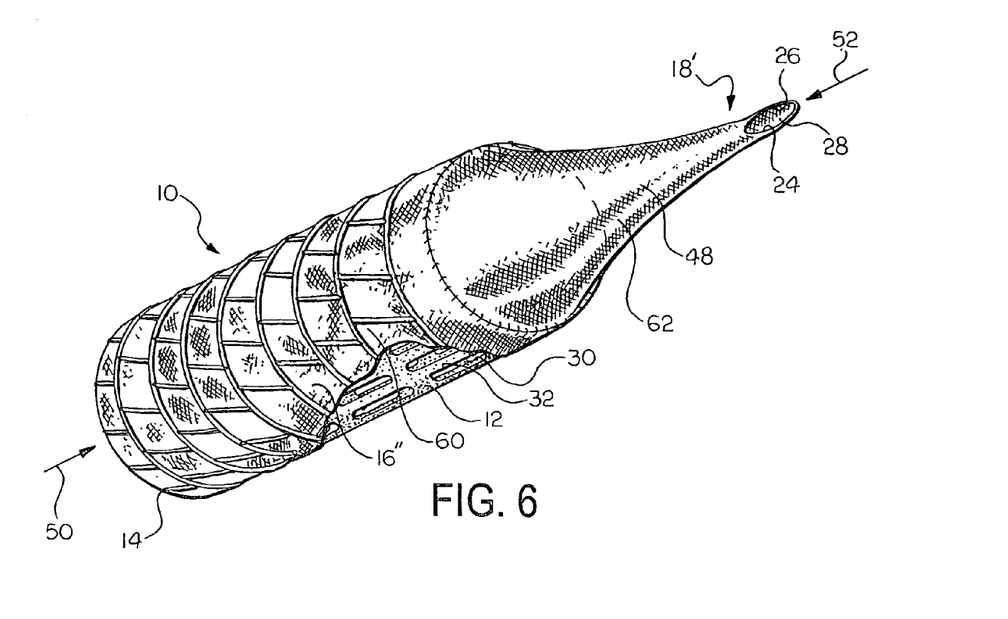
FIG. 6 is a perspective view, partially broken away, of a prosthetic valve according to a third exemplary embodiment of the invention.

In FIG. 6, the prosthetic valve 10 includes a valve 18' that comprises an evertable sleeve 48. An evertable sleeve 48 is a type of valve that comprises a portion of material, the graft member 16" in this example, that defines the opening 28. The sleeve 48 includes a first portion 60 disposed between the first 12 and second 14 frame members, and includes a second portion 62 that extends axially away from the frame members 12, 14. The sleeve 48 moves into and out of the lumen of the first frame member 12 in response to the direction of flow in the vessel in which the prosthetic valve 10 is implanted. When flow proceeds through the body vessel in a first direction, represented by arrow 50, the sleeve 48 is forced out of the lumen, as illustrated in FIG. 6, and fluid flows through the interior of the sleeve 48 and through the opening 28. When fluid flows through the body vessel in a second, opposite direction, represented by arrow 52, fluid pressure on the exterior surface of the sleeve 48 forces the sleeve 48 to evert into the lumen of the first frame member 12. In this configuration, the material of the sleeve 48 collapses upon itself, thereby substantially closing the opening 28. As a result, the valve 18' substantially prevents fluid flow through the body vessel in the second, opposite direction 52.

Figure 7:
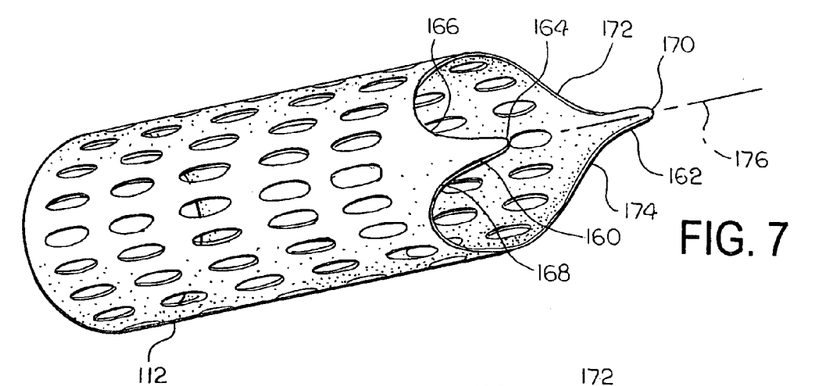
FIG. 7 is a perspective view of a frame member for use in a prosthetic valve according to an embodiment of the invention.

FIG. 7 illustrates a frame member 112 for use in a prosthetic valve according to an embodiment of the invention. The illustrated frame member 112 is suitable for use as a first frame member in a prosthetic valve according to the invention. The first frame member 112 comprises a tubular member that defines first 160 and second 162 axially-extending extension points. The axially-extending extension points 160, 162, comprise elongate portions of the first frame member 112 that extend axially away from a circumferential portion of the frame member 112. The first extension point 160 terminates at an end 164 and has curvilinear base portions 166, 168. In alternative embodiments, base positions that are substantially straight are included. The second extension point 162 also terminates at an end 170 and has curvilinear base portions 172, 174. Both extension points 160, 162 extend substantially parallel to a major axis 176 of the first frame member 112.

Figure 8:
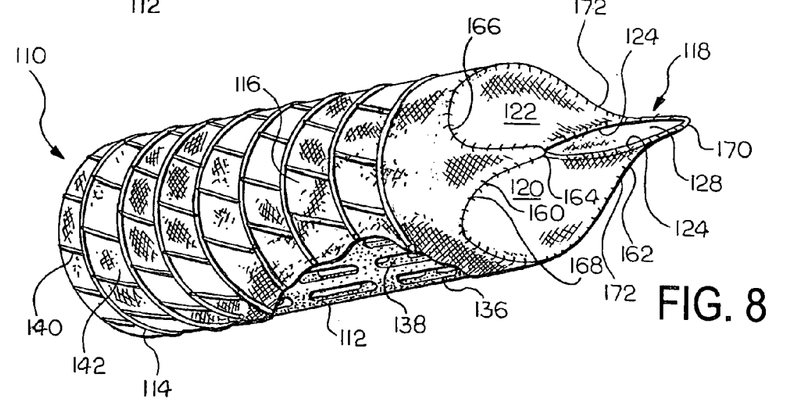
FIG. 8 is a perspective view, partially broken away, of a prosthetic valve according to a fourth exemplary embodiment of the invention that incorporates the frame member illustrated in FIG. 7.
Figure 9:
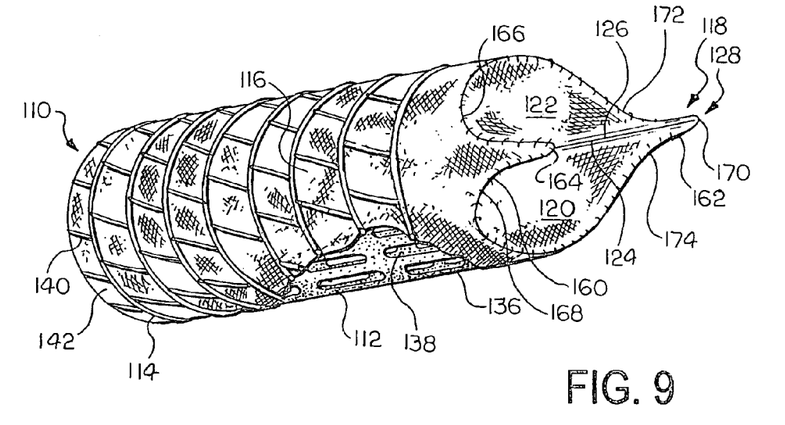
FIG. 9 is a perspective view, partially broken away, of the prosthetic valve illustrated in FIG. 8 with the valve in a closed configuration.

FIGS. 8 and 9 illustrate a prosthetic valve device 110 according to an embodiment of the invention that incorporates the first frame member 112 illustrated in FIG. 7. The prosthetic valve device 110 according to this embodiment comprises first 112 and second 114 tubular frame members and a tubular graft member 116 partially disposed between the frame members 112, 114. The graft member 116 is attached to the first frame member 112 and forms valve 118. First 120 and second 122 portions of the graft member 116 are attached to the extension points 160, 162 defined by the first frame member 112. The first portion 120 has an edge 124 that cooperates with an edge 126 of the second portion 122 to define an opening 128. FIG. 8 illustrates the opening 128 in an open configuration, in which the valve permits fluid flow through a body vessel in a first direction, while FIG. 9 illustrates the opening 128 in a closed configuration, in which the valve 118 substantially prevents fluid flow through the body vessel in a second, opposite direction. An alternative embodiment is similar to the embodiment illustrated in FIGS. 8 and 9, but includes a self-expandable inner frame member and a balloon-expandable outer frame member, as described above.

In this embodiment, the first frame member 112 comprises a balloon-expandable stent comprising a plurality of struts 136 and openings 138, while the second frame member 114 comprises a self-expandable wire frame member comprising a plurality of wire struts 140 that define a plurality of openings 142. The second frame member 114 can extend axially along the length of the first frame member 112 to the ends 164, 170 of the extension points 160, 162 of the first frame member 112. Alternatively, the second frame member 114 can extend axially to a point between the curvilinear portions 166, 168, 172, 174 and ends 164, 170 of the extension points 160, 162. Also alternatively, the second frame member 114 can extend axially along any suitable axial length of the first frame member 112, and can extend axially beyond an axial length of the first frame member 112.

Figures 10, 11:
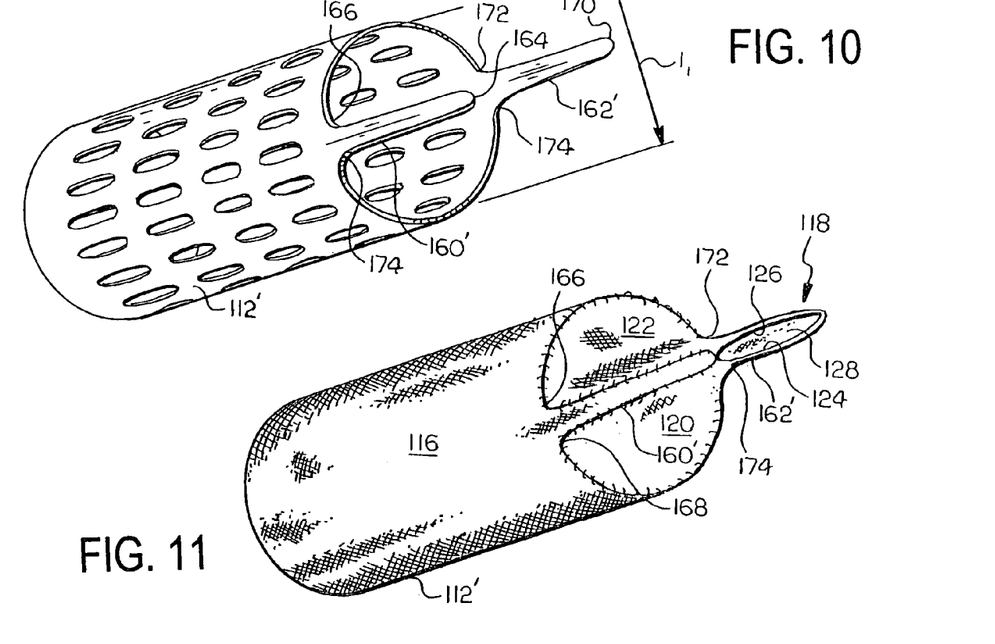
FIG. 10 is a perspective view of a frame member for use in a prosthetic valve according to an embodiment of the invention.
FIG. 11 is a perspective view of the frame member illustrated in FIG. 10 with an attached graft member.

FIG. 10 illustrates a first frame member 112' that includes first 160' and second 162' extension points having an alternative configuration. In this embodiment, the extension points 160', 162' each have a length that is greater than an inner diameter ($l_1$) of the frame member 112'. Currently contemplated lengths for the extension members in all appropriate embodiments range from between about 10% and about 1000% of the inner diameter ($l_1$) of the first frame member 112'. In exemplary embodiments, extension members have a length that is ≧50% and ≦400% of an inner diameter ($l_1$) of the first frame member 112'.

FIG. 11 illustrates the first frame member 112' of FIG. 10 with an attached graft member 116. The greater length of extension points 160', 162', as described above, may enhance the ability of the valve 118 to function by providing a greater length along which the graft portions 120, 122 coapt. This may be particularly advantageous for embodiments that include a graft material that may constrict after prolonged implantation, such as ECMs.

Figures 12, 13:
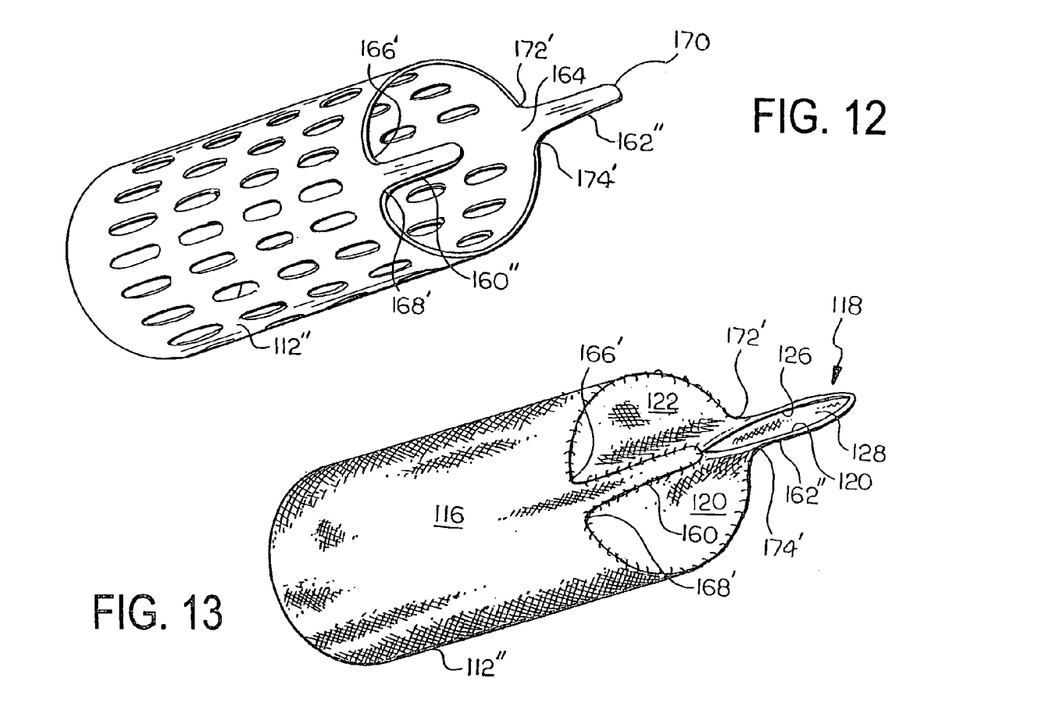
FIG. 12 is a perspective view of a frame member for use in a prosthetic valve according to an embodiment of the invention.
FIG. 13 is a perspective view of the frame member illustrated in FIG. 12 with an attached graft member.

FIG. 12 illustrates a first frame member 112" that includes first 160" and second 162" extension points having an alternative configuration. In this embodiment, the curvilinear portions 166', 168', 172', 174' are substantially right angles.

FIG. 13 illustrates the first frame member 112" of FIG. 12 with an attached graft member 116. The substantially right-angled curvilinear portions 166', 168', 172', 174' may enhance the ability of the valve 118 to function by providing an increased incidence angle at which fluid flowing in the second, opposite direction, or pressure resulting from such fluid flow, can exert force onto the graft member 116 to close the opening 128.

Figure 14:
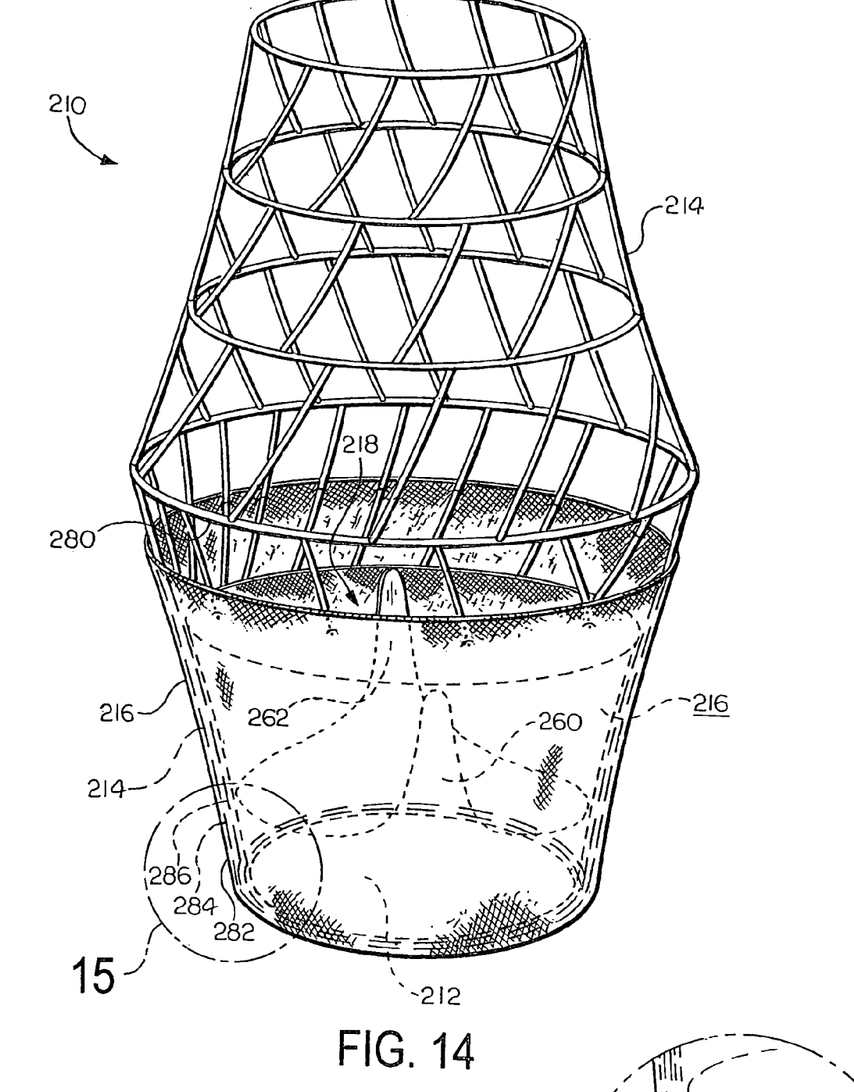
FIG. 14 is a perspective view of a prosthetic valve according to a fifth exemplary embodiment of the invention.
Figure 15:
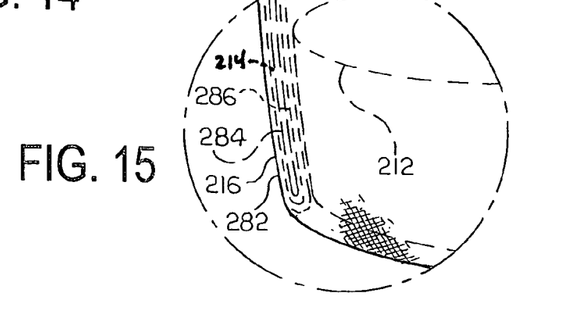
FIG. 15 is a magnified view of area 15 in FIG. 14.
Figure 16:
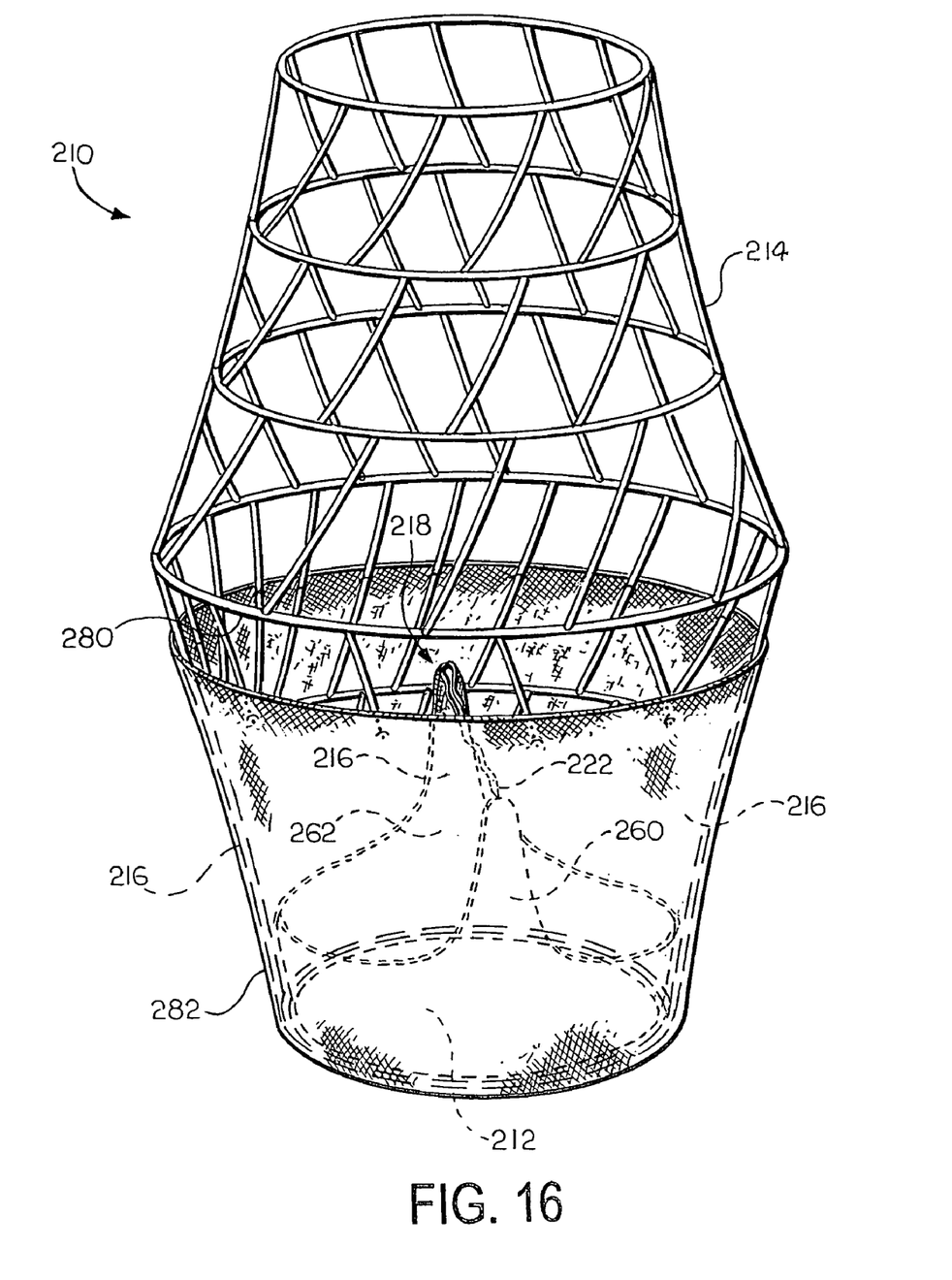
FIG. 16 is a perspective view of the prosthetic valve illustrated in FIG. 14 with the valve in a closed configuration.

FIGS. 14 through 16 illustrate a prosthetic valve 210 according to another exemplary embodiment of the invention. In this embodiment, the prosthetic valve 210 comprises a first tubular frame member 212 and a second tubular frame member 214 disposed circumferentially around the first tubular frame member 212. The second tubular frame member 214 defines a sinus portion 280. The sinus portion 280 is a portion of the second tubular frame member 214 having an enlarged resting outer diameter as compared to the remainder of the frame member 214. The presence of sinus portion 280 may provide desirable flow dynamics through the prosthetic valve 210 for facilitating clearance of the area between the second frame member 214 and the graft member 216. Also in this embodiment, the first tubular frame member 212 defines first 260 and second 262 axially-extending extension points.

The graft member 216 comprises a tubular member having a first portion 282 that is disposed on an external surface 284 of the second tubular frame member 214. The first portion 282 of the graft member 216 can be attached to the external surface 284 of the second frame member 214 by any suitable means for attaching, as described above. The graft member 216 further comprises a second portion 286 that is disposed between the first 212 and second 214 tubular frame members. The second portion 286 can be attached to the extension points 260, 262. The second portion 286 forms the valve 218 that permits fluid flow through the body vessel in a first direction and substantially prevents fluid flow through the body vessel in a second, opposite direction.

In this embodiment, the graft member 216 comprises a tubular member having a portion 286 that is inverted into the lumen of the tubular graft member 216. The inverted configuration of the graft member 216 places radially outward directed pressure on the first portion of 282 of the graft member 216 during periods of fluid flow in the second, opposite direction and/or closure of the valve 218. The radially outward directed pressure will, in turn, direct a force onto an interior wall of a body vessel in which the prosthetic valve 210 is implanted, which may aid in preventing migration of the prosthetic valve 210 in the vessel and/or prevent reflux of fluid around the valve 210. Further, if a remodellable or other natural material is used in the graft member 216, the radially outward directed force may facilitate incorporation of the first portion 282 into a wall of a body vessel in which the prosthetic valve 210 is implanted. Thus, the inverted configuration of the graft member 216 may provide effective closure of the valve 218 with a desirable seal between the prosthetic valve 210 and the interior wall of a body vessel in which the prosthetic valve 210 is implanted.

FIG. 14 illustrates the valve 218 in an open configuration, while FIG. 16 illustrates the valve 218 in a closed configuration. FIG. 15 illustrates a magnified view of area 15 in FIG. 14, showing the relationship between the graft member 216 and the first 212 and second 214 tubular frame members.

Figure 17:
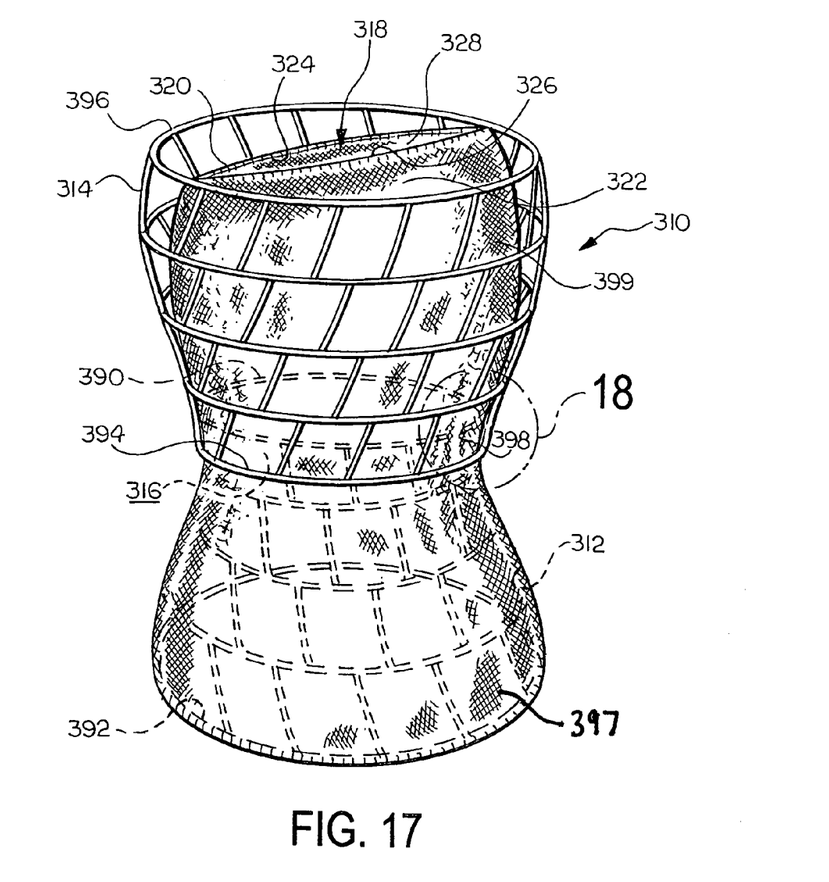
FIG. 17 is a perspective view of a prosthetic valve according to a sixth exemplary embodiment of the invention.
Figure 18:
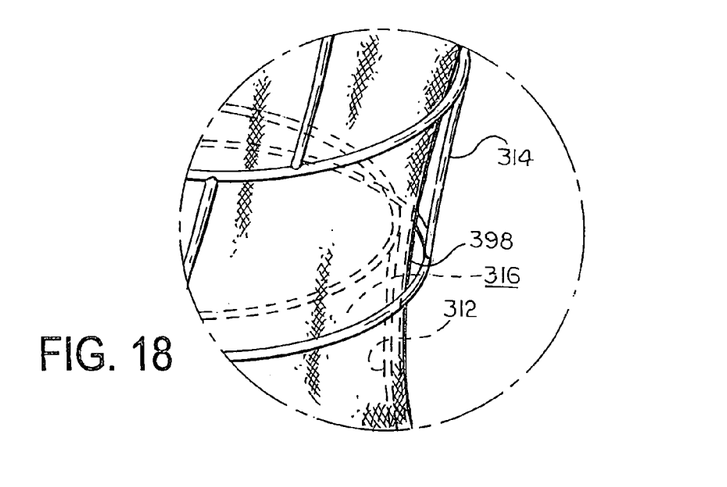
FIG. 18 is a magnified view of area 18 in FIG. 17.

FIGS. 17 and 18 illustrate a prosthetic valve 310 according to another exemplary embodiment of the invention. In this embodiment, the prosthetic valve 310 comprises a first frame member 312 having first 390 and second 392 ends, and a second frame member 314 having third 394 and fourth 396 ends. The third end 394 is disposed radially outward of the first end 390 to create an overlap region of the ends 390, 394. As illustrated in FIG. 17, the second 392 and fourth 396 ends can comprise flared ends. The presence of one or both flared ends may provide a suitable seal between the prosthetic valve 310 and the interior wall of a body vessel in which the prosthetic valve 310 is implanted. Also, a flared end creates a sinus region in the prosthetic valve 310 that may provide desirable flow dynamics through the prosthetic valve 310 for facilitating clearance of the area between the sides 320, 322 of the valve 318 and the facing portions of the frame member 314, i.e., the "valve pockets." This may reduce pooling of fluid in the valve pockets.

A first portion 398 of the graft member 316 is disposed between the first 390 and third 394 ends while a second portion 399 of the graft member 316 is disposed radially inward of the fourth end 396. A third portion 397 of the graft member 316 is disposed radially outward of the second end 392. Thus, the graft member 316 extends from an interior of the second frame member 314 to an exterior of the first frame member 312. The second portion 399 of the graft member 316 forms a valve 318 that permits fluid through the body vessel in a first direction and substantially prevents fluid flow through the body vessel in a second, opposite direction. The second portion 399 includes first 320 and second 322 sides that define edges 324, 326 that cooperatively define opening 328. The second portion 399 of the graft member 316 can be attached to the second frame member 314 using any suitable means for attaching the graft member 316 to the frame member 314. The second portion 399 can be attached to the frame member 314 in a manner that forms the valve 318. The third portion 397 is exposed for direct contact with an interior wall of a vessel in which the prosthetic valve 310 is implanted. This may facilitate anchoring of the prosthetic valve 310, particularly in embodiments in which the graft member 316 comprises a remodellable material, such as an ECM.

Figure 19:
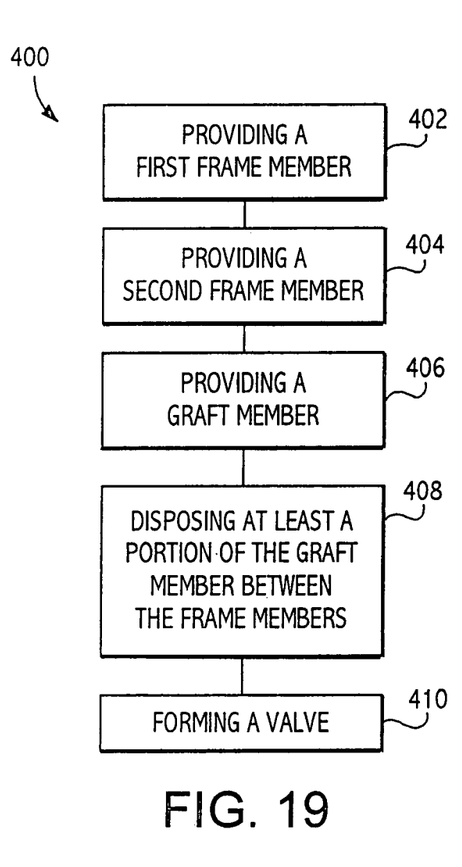
FIG. 19 is a block diagram of a method of making a prosthetic valve according to the invention.

The invention also provides methods of making prosthetic valves for implantation in body vessels. FIG. 19 is a block diagram illustrating a method 400 of making a prosthetic valve according to the invention. A step 402 of the method 400 comprises providing a first frame member. A step 404 comprises providing a second frame member. A step 406 comprises providing a graft member. A step 408 comprises disposing at least a portion of the graft member between the first and second frame members. A step 410 comprises forming a valve from a portion of the graft member. The valve is formed to permit fluid flow, when implanted in a body vessel, through the body vessel in a first direction and substantially prevent fluid flow through the body vessel in a second, opposite direction.

Figure 20:
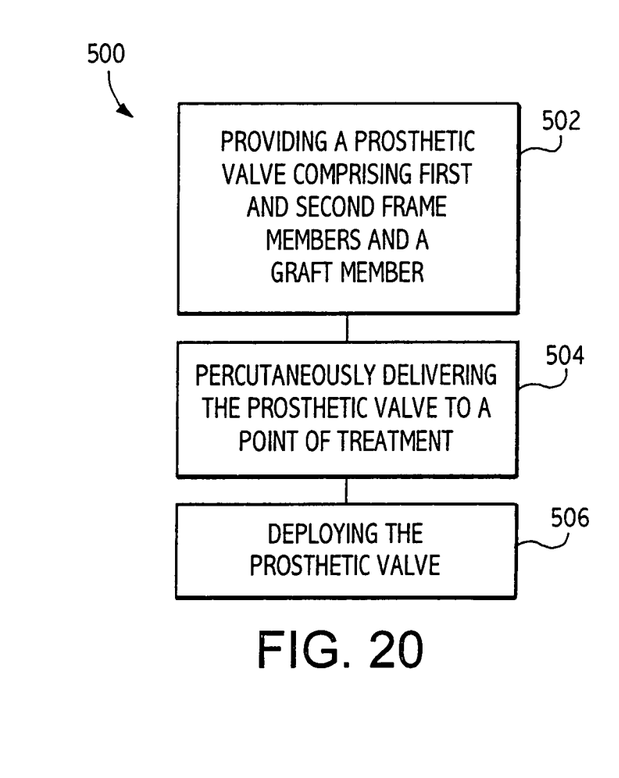
FIG. 20 is a block diagram of a method of implanting a prosthetic valve according to the invention.

The invention also provides methods of implanting prosthetic valves in a body vessel. FIG. 20 is a block diagram illustrating a method 500 of implanting a prosthetic valve according to the invention in a body vessel. A step 502 of the method 500 comprises providing a prosthetic valve comprising first and second frame members and a graft member at least partially disposed between the first and second frame members. The graft member forms a valve that, once implanted in the body vessel, can permit fluid flow through the body vessel in a first direction and substantially prevent fluid flow through the body vessel in a second, opposite direction. A step 504 comprises percutaneously delivering the prosthetic valve to a point of treatment in a body vessel. The delivering step 504 can be accomplished using any delivery device suitable for percutaneous delivery techniques, including delivery catheters and the like. A step 506 comprises deploying the prosthetic valve. The deploying step 506 can be accomplished in any manner suitable for the delivery device used in the delivering step 504.

Figure 21:
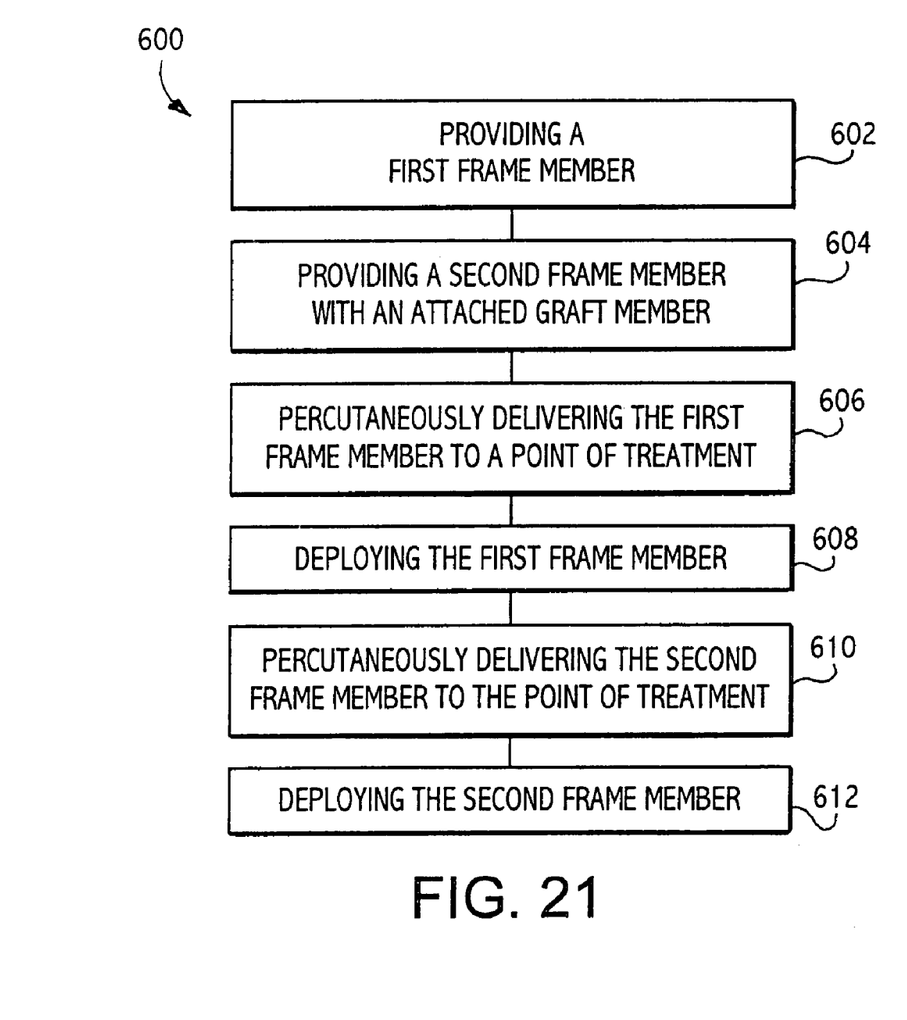
FIG. 21 is a block diagram of a method of implanting a prosthetic valve according to the invention.

FIG. 21 is a block diagram illustrating another method 600 of implanting a prosthetic valve according to the invention in a body vessel. A step 602 of the method 600 comprises providing a first frame member. A step 604 comprises providing a second frame member with an attached graft member. The graft member forms a valve that, once implanted in the body vessel, can permit fluid flow through the body vessel in a first direction and substantially prevent fluid flow through the body vessel in a second, opposite direction. A step 606 comprises percutaneously delivering the first frame member to a point of treatment in the body vessel. A step 608 comprises deploying the first frame member at the point of treatment. A step 610 comprises percutaneously delivering the second frame member with the attached graft member to the point of treatment in the body vessel. A step 612 comprises deploying the second frame member at the point of treatment. The second frame member is deployed at a position radially inward of the first frame member within the body vessel.

In all methods of implanting prosthetic valves according to the invention, percutaneous delivery steps can include the use of percutaneous delivery devices, such as catheters, dilators, sheaths, and/or other suitable endoluminal devices.

It is noted that the prosthetic valves of the invention can be placed in body vessels or other desired areas by any suitable technique, including percutaneous delivery as well as surgical placement.

The foregoing detailed description provides exemplary embodiments of the invention and includes the best mode for practicing the invention. These embodiments are intended only to serve as examples of the invention, and not to limit the scope of the invention, or its protection, in any manner.

We claim:

1. A prosthetic valve for implantation in a body vessel, comprising:
    a first frame member having a proximal end and a first external surface;
    a second frame member having a first end and a second external surface and defining a sinus portion comprising a portion having an enlarged resting outer diameter as compared to the resting outer diameter of the remainder of the second frame member, the second frame member disposed radially outward of the first frame member such that the proximal end of the first frame member and the first end of the second frame member lie in substantially the same plane; and
    a graft member forming a valve and comprising a first portion disposed between the first and second frame members, a second portion disposed substantially circumferentially about the first end of the second frame member, and a third portion disposed within the first and second frame members and forming an opening that permits fluid flow through said body vessel in a first direction and substantially prevents fluid flow through said body vessel in a second, opposite direction;
    wherein the second portion of the graft member extends along the second external surface from the first end of the second frame member to a point axially beyond the opening defined by the third portion;
    wherein the graft member has inner and outer sides, the inner side having a first portion disposed adjacent the first external surface and a second portion disposed adjacent the second external surface; and
    wherein pressure from fluid disposed between the first and second portions of the inner side of the graft member forces at least a portion of the outer side of the graft member against a portion of a wall of said body vessel;
    wherein a portion of the valve is disposed within the sinus portion.

2. A prosthetic valve according to claim 1, wherein the graft member is attached to one of the first frame member and the second frame member.

3. A prosthetic valve according to claim 1, wherein the second frame member is disposed circumferentially around the first frame member.

4. A prosthetic valve according to claim 1, wherein the second frame member comprises a self-expandable member.

5. A prosthetic valve according to claim 1, wherein the second frame member expands upon application of an outwardly directed force.

6. A prosthetic valve according to claim 1, wherein the first frame member defines an extension point and wherein the graft member is attached to the first frame member at the extension point.

7. A prosthetic valve according to claim 6, wherein the extension point has a length, the first frame member has an inner diameter, and the length is between about 10% and about 1,000% of the inner diameter.

8. A prosthetic valve according to claim 1, wherein the first and second frame members have expanded and non-expanded configurations.

9. A prosthetic valve according to claim 1, wherein the graft member comprises a bioremodellable material.

10. A prosthetic valve according to claim 1, wherein the graft member comprises an extracellular matrix material.

11. A prosthetic valve according to claim 1, wherein the graft member comprises small intestine submucosa.

12. A prosthetic valve according to claim 1, wherein the graft member comprises a tubular member.

13. A prosthetic valve according to claim 1, wherein the first frame member has a first length, the second frame member has a second length, and the first length is substantially the same as the second length.

14. A prosthetic valve according to claim 1, wherein the first frame member has a first length, the second frame member has a second length, and the second length is greater than the first length.

* * * * *